US005854031A

United States Patent [19]
Jigami et al.

[11] Patent Number: 5,854,031
[45] Date of Patent: Dec. 29, 1998

[54] MANNOSE-1-PHOSPHATE TRANSFERASE GENE FROM YEAST AND ITS USE FOR PRODUCING PHOSPHATE-CONTAINING ACIDIC SUGARS

[75] Inventors: Yoshifumi Jigami, Ushiku; Ken-ichi Nakayama, Tsukuba; Yoh-ichi Shimma, Tsukuba; Xiao-hui Wang, Tsukuba, all of Japan

[73] Assignee: Director—General of Agency of Industrial Science and Technology, Tokyo, Japan

[21] Appl. No.: 748,947

[22] Filed: Nov. 14, 1996

[30] Foreign Application Priority Data

Nov. 17, 1995 [JP] Japan .................................. 7-299509

[51] Int. Cl.$^6$ .............................. C12P 19/04; C12P 9/10; C12P 15/63; C07H 21/04
[52] U.S. Cl. ...................... 435/72; 435/193; 435/320.1; 536/23.2
[58] Field of Search .......................... 435/72, 193, 320.1; 536/23.2

[56] References Cited

U.S. PATENT DOCUMENTS 3,713,979  1/1973  Slodki et al. .............................. 195/31
5,135,854  8/1992  MacKay et al. ........................ 435/69.1

OTHER PUBLICATIONS

Winnett, E. et al. EMBL Database, Accession No. S61089, available Oct., 1995.
Wang et al. (1995) "Molecular cloning of MNN6 gene involved in mannosylphosphate addition in yeast mannan" Nippon Bunshi Seibutsu Gakkai Nenkai Puroguramu, Koen Yoshishu, vol. 18, p. 390 Abstract 1P–525.
Alberts, b. et al. Molecular Biology of the Cell, Second Edition. New York, Garland Publishing, Inc., 1989, pp. 258–262, 265, 266.
E. M. Karson et al., "Biosynthesis of Yeast Mannan," The Journal of Biological Chemistry, vol. 1253, No. 18, Issue of Sep. 25, 1978, pp. 6484–6492, Printed in U.S.A.

Primary Examiner—Kawai Lau
Attorney, Agent, or Firm—Fish & Richardson, P.C.

[57] ABSTRACT

The present invention relates to a mannose-1-phosphate transferase gene from yeast (*Saccharomyces cerevisiae*), a process for producing a mannose-1-phosphate-containing acidic sugar chain which comprises culturing yeast cells transformed with a plasmid DNA containing said gene, obtaining mannose-1-phosphate transferase from the culture, and allowing the enzyme to act on a neutral core sugar chain in vivo or in vitro, and a process for producing a phosphate-containing acidic sugar chain which comprises removal of a mannose moiety by acid-treatment of said mannose-1-phosphate-containing acidic sugar chain. According to the present invention, an acidic sugar chain having mannose-1-phosphate added to the same neutral core sugar chain as a high mannose type sugar chain produced by mammalian (e.g. human) cells can be produced in large amounts with high purity by genetic engineering means using yeast. Further, an acidic sugar chain identical with a useful phosphate-containing core sugar chain derived from human, which can function as a labeling marker for transport of glycoproteins into lysosomes in mammalian (e.g. human) cells, can be produced in large amounts with high purity.

4 Claims, 8 Drawing Sheets

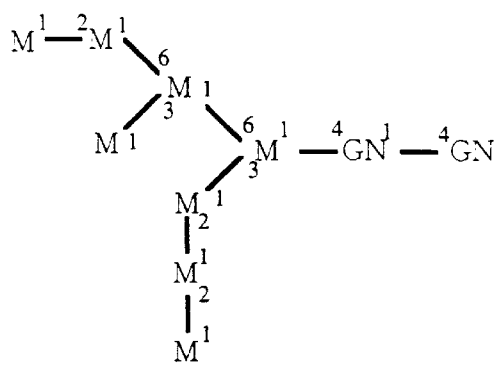
Formula 1
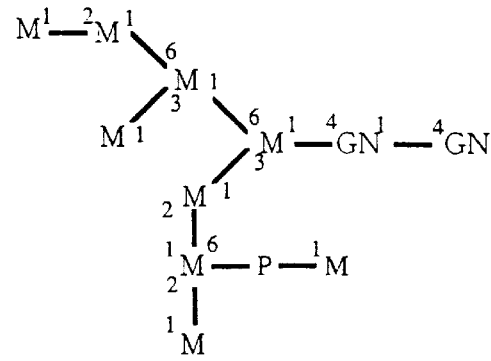
Formula 2
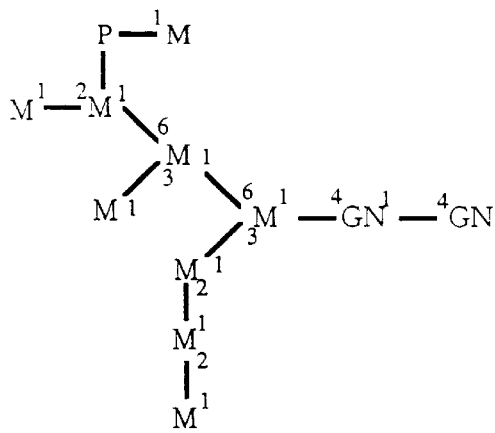
Formula 3
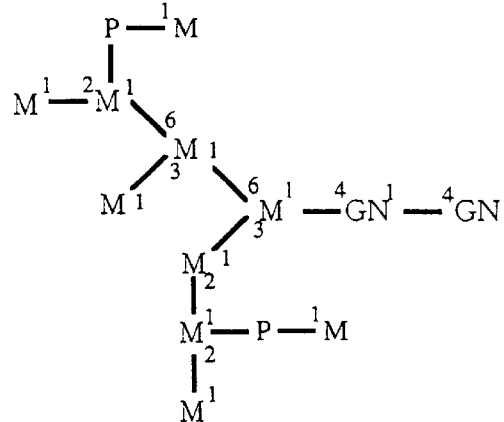
Formula 4
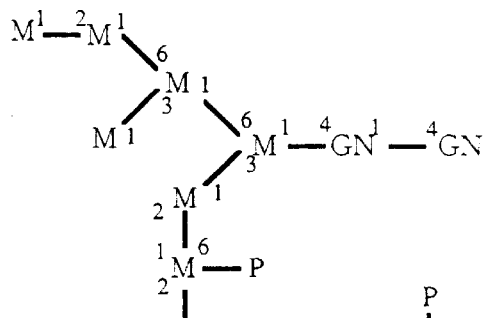
Formula 5
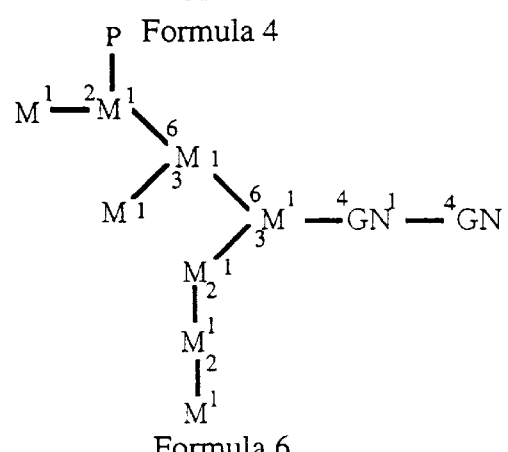
Formula 6
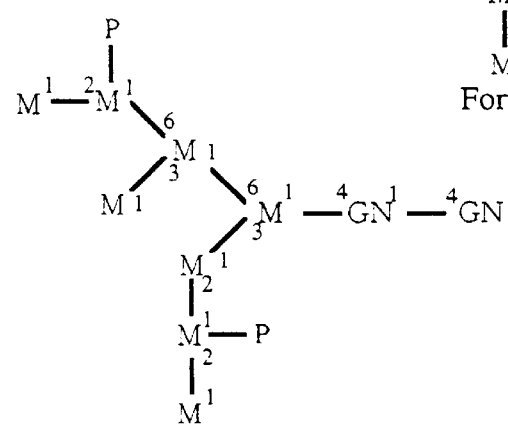
Formula 7
FIG. 1

```
ATGCACGTACTGCTGAGCAAAAAAATAGCACGCTTTCTGTTGATTTCGTTTGTTTTCGTG
 M  H  V  L  L  S  K  K  I  A  R  F  L  L  I  S  F  V  F  V

CTTGCGCTAATGGTGACAATAAATCATCCAAAAACAAAGCAGATGTCTGAACAGTATGTT
 L  A  L  M  V  T  I  N  H  P  K  T  K  Q  M  S  E  Q  Y  V

ACACCATACCTTCCGAAATCTTTGCAACCTATTGCAAAAATTAGTGCAGAGGAACAAAGG
 T  P  Y  L  P  K  S  L  Q  P  I  A  K  I  S  A  E  E  Q  R

CGTATACAAAGTGAACAGGAAGAAGCCGAATTGAAGCAATCTTTAGAGGGAGAGGCCATT
 R  I  Q  S  E  Q  E  E  A  E  L  K  Q  S  L  E  G  E  A  I

AGAAATGCCACCGTGAATGCCATTAAGGAAAAGATCAAATCTTATGGTGGTAATGAAACG
 R  N  A  T  V  N  A  I  K  E  K  I  K  S  Y  G  G  N  E  T

ACGCTAGGGTTCATGGTGCCATCGTATATCAATCATAGAGGATCACCACCAAAGGCGTGC
 T  L  G  F  M  V  P  S  Y  I  N  H  R  G  S  P  P  K  A  C

TTTGTCTCACTAATTACTGAAAGGGATTCCATGACCCAAATCTTACAATCTATTGATGAA
 F  V  S  L  I  T  E  R  D  S  M  T  Q  I  L  Q  S  I  D  E

GTGCAGGTGAAGTTTAACAAAAATTTTGCTTATCCTTGGGTTTTTATTAGTCAGGGGGAG
 V  Q  V  K  F  N  K  N  F  A  Y  P  W  V  F  I  S  Q  G  E

CTTGACGGAATGAAGCAAGAAATGATTCGTCAAGCCATAACTGATTCTATGAATGGTGAT
 L  D  G  M  K  Q  E  M  I  R  Q  A  I  T  D  S  M  N  G  D

CCTGAGTTAATTAATATTAAATTTGCTGAAATTCCTGCAGACGAATGGGTATACCCTGAA
 P  E  L  I  N  I  K  F  A  E  I  P  A  D  E  W  V  Y  P  E

TGGATTGATGAAAATAAAGCAGCAGAATCGCTAATTTCATTAGCAAATGTACCGGATGGT
 W  I  D  E  N  K  A  A  E  S  L  I  S  L  A  N  V  P  D  G

GATTCTAGAGCTGTAAGATATCAAGCTAGATATTTTGCAGGGTTTTTTTGGAGGCATCCA
 D  S  R  A  V  R  Y  Q  A  R  Y  F  A  G  F  F  W  R  H  P

GTTCTGGATGAGTTTGATTGGTACTGGAGAGTAGACCCTGGTATTAAATTGTACTGTGAT
 V  L  D  E  F  D  W  Y  W  R  V  D  P  G  I  K  L  Y  C  D

ATTGATCATGACCTTTTTAGGTGGATGCAAGATGAAGGCAAAGTGTTTGGTTTCACATTG
 I  D  H  D  L  F  R  W  M  Q  D  E  G  K  V  F  G  F  T  L

AGTATGAGTGAAGCTAAGGAAGCCAATGAGAAGATTTGGGATGTTACGAAAAAATTTGCA
 S  M  S  E  A  K  E  A  N  E  K  I  W  D  V  T  K  K  F  A

AAGGATTTTCCAAAGTTTATTTCCGAGAATAATTTCAAGTCATTTATTACAAAAAAGGAC
 K  D  F  P  K  F  I  S  E  N  N  F  K  S  F  I  T  K  K  D

TCTGAAGATTTTAACAACTGTGAATTCACATCAAATTTTGAAATTGGTAATTTGAACTTT
 S  E  D  F  N  N  C  E  F  T  S  N  F  E  I  G  N  L  N  F

TATAGATCGCCAGCTTACAGGAAATTTTTTAATTACATCGACGAAGAGGGCGGTATTTTC
 Y  R  S  P  A  Y  R  K  F  F  N  Y  I  D  E  E  G  G  I  F

TACTGGAAATGGTCTGATTCCATCATCCACACAATTGGGTTATCGATGCTGTTGCCAAAG
 Y  W  K  W  S  D  S  I  I  H  T  I  G  L  S  M  L  L  P  K

GATAAAATACATTTTTTCGAAAATATAGGATTCCATTATGACAAGTACAATAACTGTCCC
 D  K  I  H  F  F  E  N  I  G  F  H  Y  D  K  Y  N  N  C  P

CTAAACGATGATATATGGAACCAATATAATTGTAACTGTGACCAGGGTAACGATTTCACG
 L  N  D  D  I  W  N  Q  Y  N  C  N  C  D  Q  G  N  D  F  T

TTTAGAAGTGGTTCATGTGGCGGACATTACTTCGACATTATGAAGAAAGATAAGCCAGAA
 F  R  S  G  S  C  G  G  H  Y  F  D  I  M  K  K  D  K  P  E

GGTTGGGATAGGTTACCATAAATCAAAACACTGATGTATAAGAACAATAATCTTCTACAT
 G  W  D  R  L  P  *
```

FIG. 5

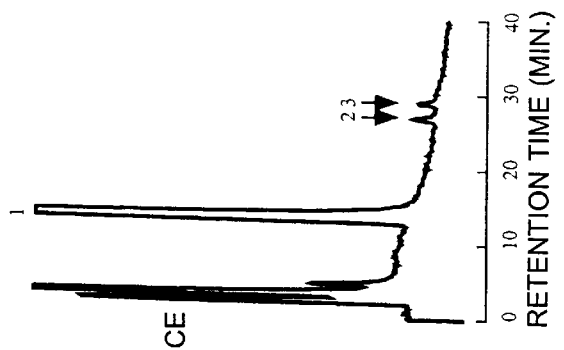
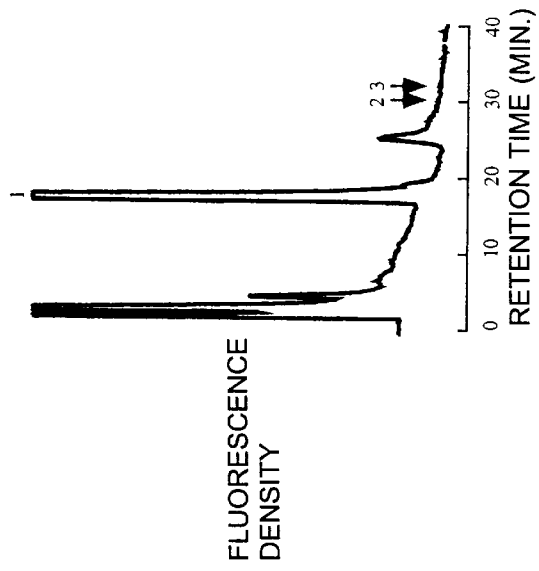
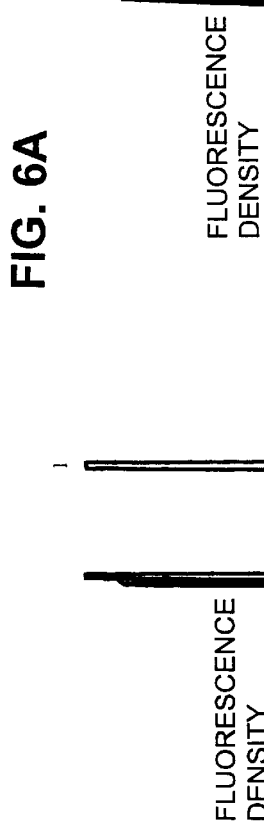

ent invention relates to a mannose-1-phosphate
MANNOSE-1-PHOSPHATE TRANSFERASE GENE FROM YEAST AND ITS USE FOR PRODUCING PHOSPHATE-CONTAINING ACIDIC SUGARS

FIELD OF THE INVENTION

The present invention relates to a mannose-1-phosphate transferase gene from yeast and a process for production, by use of said gene, of phosphate-containing acidic sugar chains capable of functioning as a labeling marker for transport of glycoproteins to lysosomes in mammalian (e.g. human) cells.

BACKGROUND OF THE INVENTION

Many proteins with important functions in vivo are not simple proteins but glycoproteins with sugar chains. Such proteins will lose their original biological activities upon removal of their sugar chains as revealed by erythropoietin (EPO), tissue plasminogen activator (TPA) etc. (Akira Kobata, "Tanpakushitsu Kakusan Kouso" (Protein, Nucleic Acid and Enzyme), vol. 36, p. 775 (1991); Makoto Takeuchi, "Seikagaku" (the Journal of Japanese Biochemical Society), vol. 62, p. 1272 (1990)), and it is suggested that such sugar chains play an important role in expression of biological activities. Although there are many types of glycoproteins derived from mammals including humans, sugar chains added to glycoproteins differ in their structure depending on the type of protein, biological species and internal organs from which they are derived, while their chain lengths are not uniform and heterogeneous with a certain chain length distribution (Akira Kobata, "Tanpakushitsu Kakusan Kouso" (Protein, Nucleic Acid and Enzyme), vol. 36, p. 775 (1991); Makoto Takeuchi, "Seikagaku" (the Journal of Japanese Biochemical Society), vol. 62, p. 1272 (1990)). Therefore, it is still not elucidated how in sugar chains their biological activity is related to their structure, and each protein should be dealt with by trial and error at present to elucidate the type and structure of sugar chains added to protein moieties. Hence, there is demand for developments in techniques by which the structure (including type of sugar, binding position, chain length, etc.) of sugar chains added to proteins can be modified and controlled as desired. Supplying of sugar chains of uniform chain length with a definite chemical structure, together with glycoproteins to which such sugar chains are added, is hoped for not only in the academic world but also in the industrial world.

The sugar chains bound to proteins are divided into 2 types i.e. N-linked type bound via an asparagine residue and O-linked type bound via a serine or threonine residue to the proteins. Among these, the N-linked sugar chain has been elucidated for its biosynthetic pathway and there are many findings. According to them, the biosynthesis of a sugar chain begins in the endoplasmic reticulum (ER) and then the sugar chain undergoes modifications in the Golgi apparatus. It was found that there is no essential difference between yeast and mammalian cells in the sugar chain formed in the ER. This sugar chain is referred to hereinafter as core sugar chain, found to be $Man_8GlcNAc_2$ consisting of 8 molecules of mannose (Man) and 2 molecules of N-acetylglucosamine (GlcNAc) (FIG. 1, Formula 1). A protein with $Man_8GlcNAc_2$ as the core sugar chain is transported to the Golgi apparatus where it undergoes various modifications. In these modifications in the Golgi apparatus, there is a significant difference between yeast and mammalian cells (Kukuruzinska et al., Ann. Rev. Biochem., vol. 56, p. 915 (1987)).

In mammalian cells, the modification of the sugar chain will proceed via 3 different pathways depending on the protein moiety to which it is added. That is, (1) the core sugar chain does not change, (2) the core sugar chain is converted into Man-6-P-1-GlcNAc by adding the N-acetylglucosamine-1-phosphate moiety (GlcNAc-1-P) in UDP-N-acetyl glucosamine (UDP-GlcNAc) to the 6-position of Man in the core sugar chain, followed by removing the GlcNAc moiety to form an acidic sugar chain in the glycoprotein, and (3) the core sugar chain is converted into $Man_3GlcNAc_2$ by sequentially removing 5 Man molecules, following or followed by sequentially adding GlcNAc, galactose (Gal), N-acetylneuraminic acid (also called sialic acid (NeuNAc)) etc. to form various, mixed or complex sugar chains (R. Kornfeld and S. Kornfeld, Ann. Rev. Biochem., vol. 54, pp. 631–664 (1985)).

On the other hand, it was found that in yeast a large number of Man molecules are added to said core sugar chain ($Man_8GlcNAc_2$) to form so-called "outer chain". It was further found that mannnose-1-phosphate molecules are added to the core sugar chain and the sugar outer chain moieties to give acidic sugar chains (see FIG. 2). These modifications in yeast differ from those in animal cells. It was reported that unlike animal cells these modifications in yeast do not confer a sorting signal on glycoproteins localized in vacuoles (organelle corresponding to lysosomes in animal cells). Therefore, the physiological function of these phosphorylated sugar chains in yeast remains unclear (Kukuruzinska et al., Ann. Rev. Biochem., vol. 56, p. 915 (1987)).

The phosphorylation sites on the mannose phosphate-containing sugar chains in yeast can be divided into 4 types. That is, as shown in FIG. 2, G, phosphate addition occurs at the α-1,3-branch side (1) and α-1,6-branch side (2) of the core sugar chain ($Man_8GlcNAc_2$) synthesized in the ER, and at the α-1,2-branch side (3) present abundantly in the mannose outer chain and at the non-reduced terminal (4) of the mannose outer chain synthesized in the Golgi apparatus (A. Herscovics and P. Orlean, FASEB J., vol. 7, pp. 540–550 (1993)). It is noted though not confirmed with data that the mannosyl phosphate-containing sugar chain may participate in intercellular agglutination and localization of glycoproteins such as invertase etc. in a cell surface layer of yeast.

The biosynthesis of the sugar outer chain in yeast is believed to proceed through a pathway as shown in FIG. 2 (Ballou et al., Proc. Natl. Acad. Sci. U.S.A., vol. 87, p. 3368 (1990)). That is, one Man molecule is added to the core sugar chain via α-1,6-linkage to initiate chain elongation (FIG. 2, I) and Man molecules are further added via α-1,6-linkage to elongate the chain (FIG. 2, II) to form a poly-α-1,6 Man linkage as a sugar outer chain skeleton (FIG. 2, E). These Man molecules bound to one another via α-1,6-linkage possess Man branches bound via α-1,2-linkage (FIG. 2, F), usually with their terminals having Man molecules bound to one another via α-1,3-linkage (see FIG. 2, G).

However, the Man at the terminal of α-1,6-linkage has only one Man molecule bound to it via α-1,2-linkage, and no additional Man will be added via α-1,3-linkage to said α-1,2-bound Man molecule (FIG. 2, F or G) (Gopal and Ballou, Proc. Natl. Acad. Sci. U.S.A., vol. 84, p. 8824 (1987)). Therefore, the production of the core sugar chain can be attained by isolating a mutant not permitting addition of any sugar outer chain to terminate sugar chain synthesis upon completion of said sugar core chain (FIG. 2, A). The present inventors have successfully prepared a mutant not permitting any sugar outer chain to be added (Japanese Patent Application LOP Publication No. 277,086/1994). However, it was found that the sugar chains of glycoproteins produced in this method contain acidic sugar chains (FIG. 1, Formulae 2 to 4) in addition to a neutral sugar chain (FIG. 1, Formula 1) (12th Biotechnology Symposium Preliminary Collection, pp. 153–157, published on Oct. 14, 1994 by "Biotechnology Kaihatsu Gijutsu Kenkyu Kumiai" (Biotechnology Development Research Association)). The acidic sugar chains are not inherent in the sugar chains derived from mammals including humans. In mammalian cells, GlnNAc-1-phosphate (not mannose-1-phosphate) is added to the addition sites for mannose-1-phosphate shown in Formulae 2 to 4, which is followed by removing the GlcNAc moieties therefrom, resulting in the acidic sugar chains shown in FIG. 1, Formulae 5 to 7.

In yeast cells, however, there does not occur the removal of the Man moieties from the acidic sugar chains shown in FIG. 1, Formulae 2 to 4. Hence, it is suggested that the sugar chains shown in Formulae 2 to 4 are recognized as foreign (antigenic) substances in mammals (Clinton E. Ballou, Methods in Enzymology, vol. 185, pp. 440 to 470 (1990)).

Because there is a significant difference in the structure of sugar chains in glycoproteins between yeast and mammalian cells as described above, it is noted that even if useful glycoproteins derived from mammals such as humans are produced in yeast by genetic engineering means, such glycoproteins differ from those of mammals in their biological activities and antigenicity due to their different sugar chains. Therefore, the production of mammal-derived glycoproteins by yeast was difficult in the prior art.

The acidic sugar chains (FIG. 1, Formulae 5 to 7), converted from said core sugar chain in mammalian cells, act as a labeling marker for transporting their glycoproteins to lysosomes in mammalian (e.g. human) cells. Therefore, the acidic sugar chain is useful as a labeling sugar chain for glycoproteins and various useful drugs for their localization in specific organelles (lysosomes) in cells by utilizing drug delivery techniques e.g. through their inclusion in liposomes. At present, however, the acidic sugar chain as well as glycoproteins containing it are difficult to supply uniformly in large amounts.

Therefore, it is desired to overcome the disadvantages in the production of N-linked glyco proteins derived from humans and other mammals.

SUMMARY OF THE INVENTION

The object of the present invention is to provide a production process in which said useful phosphate-containing acidic sugar chain whose structure is the same as in mammalian cells can be produced in large amounts by recombinant DNA technology.

As a result of their eager research, the present inventors successfully isolated a mannose-1-phosphate transferase gene (MNN6 gene) involved in mannnose-1-phosphate addition reaction that is a yeast-specific sugar chain modification. They further determined the structure of this gene, and they successfully utilized this gene to produce the acidic sugar chain. This acidic sugar chain has one or two phosphate molecules added to the same high mannose type neutral sugar chain as in mammals such as humans, and it is free from an antigenic mannose-1-phosphate-containing acidic sugar chain.

That is, the present invention encompasses:

1. A mannose-1-phosphate transferase gene from yeast (Saccharomyces cerevisiae) coding substantially for the amino acid sequence of SEQ ID NO:2)

2. A mannose-1-phosphate transferase gene from yeast (Saccharomyces cerevisiae) described in 1, which is represented by the nucleotide sequence of SEQ ID NO:1;

3. A plasmid DNA containing the whole or a part of the mannose-1-phosphate transferase gene from yeast described in 1 or 2 above;

4. A process for producing a mannose-1-phosphate-containing sugar chain, which comprises culturing yeast cells transformed with the plasmid DNA described in 3 above, obtaining mannose-1-phosphate transferase from the culture, and allowing the enzyme to act on a neutral core sugar chain in vivo or in vitro; and 5. A process for producing a mannose-1-phosphate-containing sugar chain, which comprises acid-treating the mannose-1-phosphate-added acidic sugar chain obtained in the process described in 4 above to remove its mannose moiety.

In the present invention, the process for producing in yeast the mannose-1-phosphate acidic sugar chain having mannose-1-phosphate added to the same high mannose type neutral sugar chain as in mammals, consists of the following steps:

(1) obtaining a gene coding for mannose-1-phosphate transferase (MNN6 gene);

(2) introducing the MNN6 gene into a yeast expression vector (pRS316, YEp352 etc.) to construct a plasmid for expression of the MNN6 gene;

(3) introducing the plasmid into a yeast host which is a double mutant having OCH1 gene destroyed and a mutation on MNN1 gene (mnn1) to express mannose-1-phosphate transferase with which the neutral sugar chain of Formula 1 in FIG. 1 is converted in vivo into a mannose-1-phosphate-containing acidic sugar chain; and (4) isolating and purifying the sugar chain from glycoproteins (manno-proteins) in a cell surface layer of organisms obtained by culturing the transformant in (3) above.

The present process for producing the phosphate-containing acidic sugar chain having phosphate added to the same high mannose type neutral sugar chain as in mammals, consists of the following steps:

(1) obtaining a gene coding for mannose-1-phosphate transferase gene (MNN6 gene);

(2) introducing the MNN6 gene into a yeast expression vector (pRS316, YEp352 etc.) to construct a plasmid for expression of the MNN6 gene;

(3) introducing the plasmid into a yeast host which is a double mutant having OCH1 gene destroyed and a mutation on MNN1 gene (mnn1) to express mannose-1-phosphate transferase with which the neutral sugar chain of Formula 1 in FIG. 1 is converted in vivo into a mannose-1-phosphate-containing acidic sugar chain; and (4) allowing disrupted organisms as an enzyme source of mannose-1-phosphate transferase from the yeast obtained step (3) above to react in vitro with a neutral core sugar chain and then recovering the reaction product having mannose-1-phosphate added to it; and (5) treating the product in (3) or (4) above with an acid (treatment with 0.01N HCl at 100° C. for 30 minutes) to remove the mannose moiety from the mannose-1-phosphate residue to convert it into a phosphate-containing sugar chain. This phosphate-containing acidic sugar chain is useful as a labeling marker for selective transport of drugs or proteins to lysosomes in mammalian (e.g. human) cells.

BRIEF DESCRIPTION OF THE DRAWINGS

FIG. 1 shows the structures of a core sugar chain and its modified sugar chains formed in yeast and mammalian cells.

FIG. 5 shows a nucleotide sequence containing the MNN6 gene and its coding amino acid sequence.

FIG. 6 shows mannose-1-phosphate transferase activities by several yeast mutants.

A: Strain (TO5-2B/pRS316) prepared by introducing a control plasmid to a triple mutant (Δoch1 mnn1 mnn6 his1 and/or his3 ura3).

B: Double mutant T05-2C (Δoch1 mnn1 ura3).

C: Strain (TO5-2B/pRS-MNN6) prepared by introducing a plasmid containing 1 copy of MNN6 gene to a triple mutant (Δoch1 mnn1 mnn6 his1 and/or his3 ura3).

Figure 7:
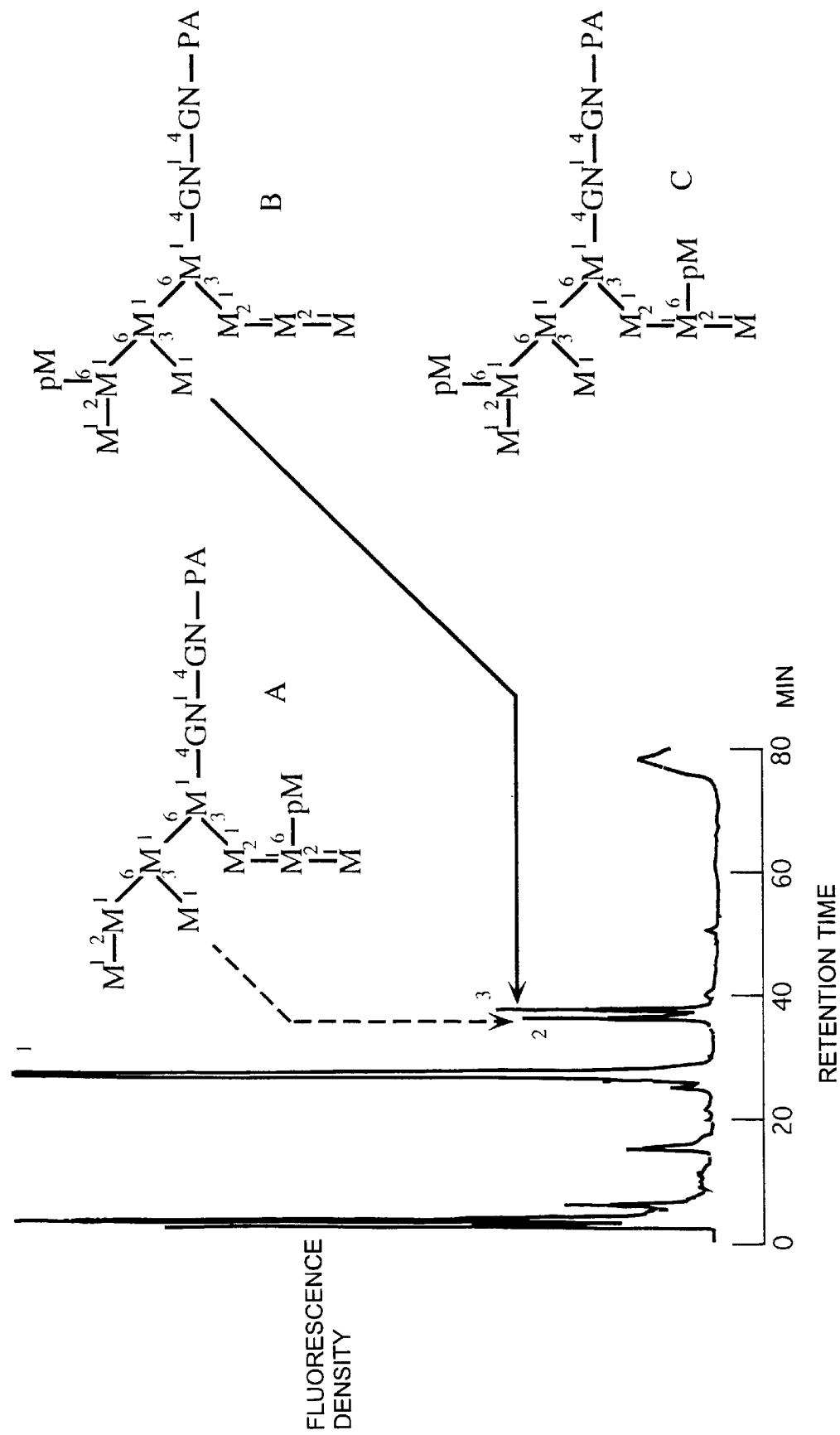

FIG. 7 shows HPLC analysis and structures of enzymatic reaction products.

Figure 8A:
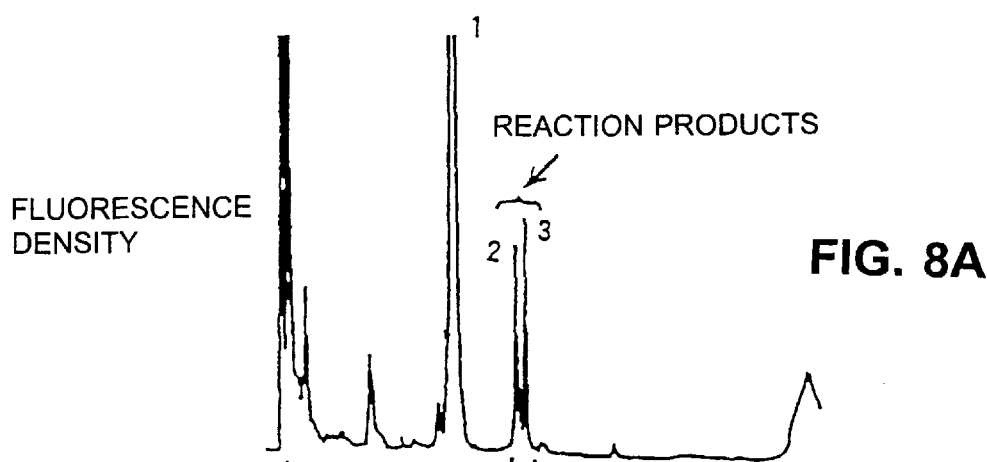
Figure 8B:
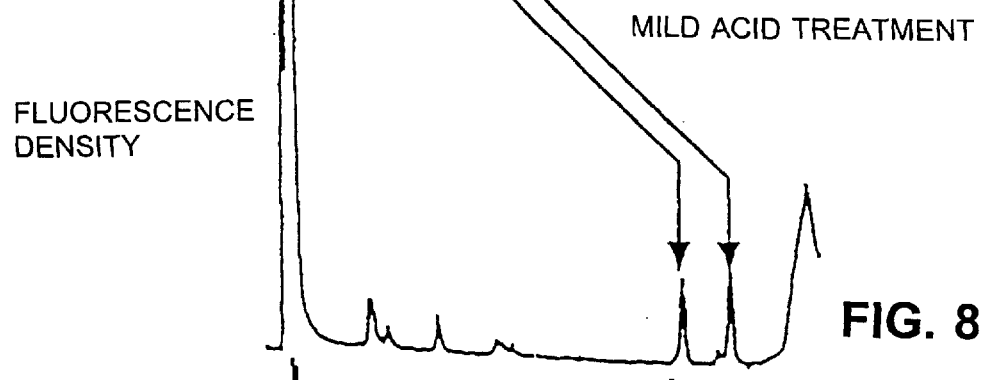
Figure 8C:
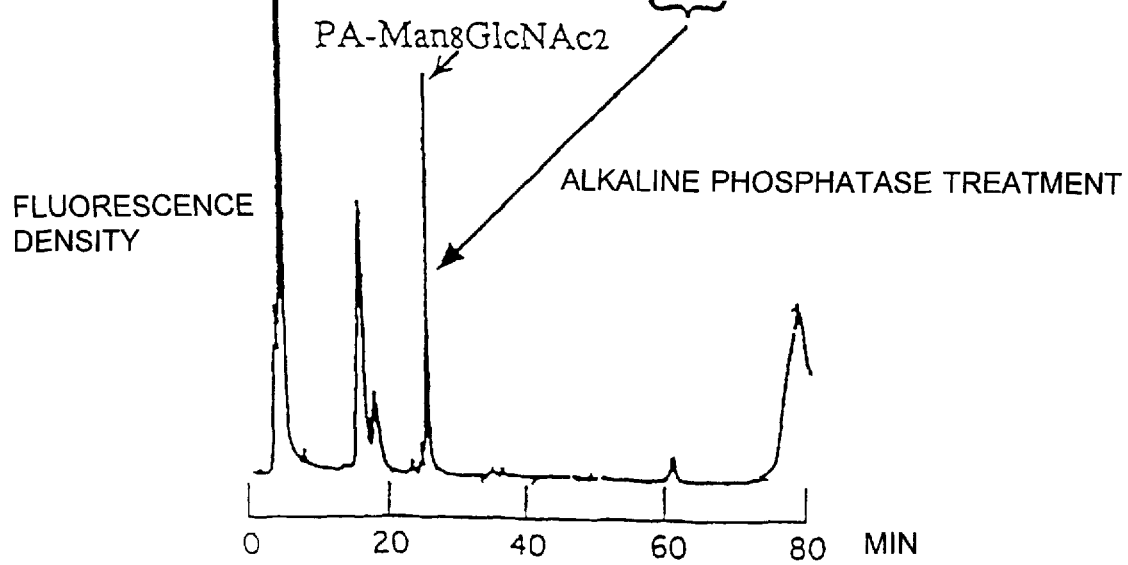

FIG. 8 shows HPLC analysis of acid-treated and alkaline phosphatase-treated enzymatic reaction products.

A: Reaction products.

B: Acid-treated products.

C: Alkaline phosphatase-treated products.

DETAILED DESCRIPTION OF THE INVENTION

Hereinafter, the present invention is described in detail. The amino acid and nucleotide sequences in the present specification are given abbreviations in accordance with the regulation of IUPAC-IUB or by conventional nomenclature in this field.

1. Isolation and purification of a mannose-1-phosphate transferase gene

The preparation of the mannose-1-phosphate transferase gene of the present invention involves extracting a genomic DNA from *Saccharomyces cerevisiae* by usual means to prepare a gene library, selecting the target DNA from the library, introducing it into host yeast cells reported to have their mannose phosphate content significantly lowered, selecting transformed yeast cells having their mannose phosphate content recovered levels of wild-type cells.

The extraction of the genomic DNA from *Saccharomyces cerevisiae* can be effected by a conventional method as described for example by D. R. Cryer et al. (Methods in Cell Biology, vol. 12, p. 39 (1975)) and P. Philippsen et al. (Methods in Enzymology, vol. 194, p. 169 (1991)).

The gene library can be prepared in a usual manner using conventional vectors such as plasmid vectors, lambda phage vectors etc., or cosmid vectors etc. enabling cloning of larger DNA fragments by virtue of their phage- and plasmid-like properties.

Host cells into which the DNA is introduced are typically a mnn6 mutant of *Saccharomyces cerevisiae*, available from Dr. Ballou, Department of Molecular and Cell Biology, University of California, Berkeley, U.S.A. (see Clinton E. Ballou, Methods in Enzymology, vol. 185, pp. 440–470 (1990)).

Two types of yeast mutant with about 90% reduction in phosphorylation in sugar outer chain moieties were isolated (E. M. Karson and C. E. Ballou, J. Biol. Chem., vol. 253, pp. 6484–6492 (1978)). Among them, mnn4 and mnn6 mutants were judged in dye-binding assays with alcian blue to be dominant and recessive, respectively, each having a single mutation. The phosphate group is a major negative charge group in the cell wall, and alcian blue is conveniently used as a basic phthalocyanin type dye to evaluate the degree of phosphorylation of mannoprotein. Haploid mnn6 cells grown in YEPD medium do not bind to alcian blue dye (C. E. Ballou, Methods in Enzymology, vol. 185, pp. 440–470 (1990)).

Therefore, the ability of mnn6 mutant to bind to said dye is much lower than that of wild type cells, so this difference can be used to isolate the wild-type gene corresponding to the mutation.

To introduce DNA into cells to be transformed, e.g. *E. coli* is be infected as host in a usual manner with e.g. phage as vector, so that the DNA can be efficiently integrated into the host and the gene can thereby be amplified. Alternatively, yeast cells can be transformed with a plasmid by treatment with a lithium salt or by electric treatment to facilitate their incorporation of the plasmid.

After each step, the DNA can be isolated and purified in any conventional method. The DNA of the invention can be determined for its sequence in a conventional method such as the dideoxy method (Sanger, F. et al., Proc. Natl. Acad. Sci., U.S.A., 74, 5463–5467 (1977)). Alternatively, the DNA can easily be sequenced using a commercial sequencing kit or the like.

The mannose-1-phosphate transferase gene of the present invention codes substantially for the amino acid sequence of SEQ ID NO:2 or is represented by the nucleotide sequence of SEQ ID NO:1. By the term "tsubstantially" it is meant that in said amino acid sequence, amino acid(s) may undergo deletion, replacement, addition, polymerization etc. Hence, the present invention encompasses equivalents of the mannose-1-phosphate transferase of said amino acid sequence, as well as genes thereof. For example, the mannose-1-phosphate transferase of the present invention may have been subjected by genetic engineering means to deletion of the N-terminal amino acid residue (Met) or to posttranslational modifications (addition, deletion, replacement etc.). The genetic engineering means include various methods such as site specific mutagenesis for DNA modifications.

Polymerase chain reaction (PCR) techniques are those permitting a target DNA region to be specifically amplified 10- to 1000,000-fold in vitro for about 2 to 3 hours with sense- and anti-sense primers surrounding the target region, thermostable Taq polymerase, DNA amplification system, etc. The gene of the present invention, or a partial fragment thereof, can be amplified by PCR techniques, and the DNA thus amplified can be used to introduce various modifications or gene disruption into the MNN6 gene.

The MNN6 gene can be mutated in this manner to prepare a yeast mutant (mnn6) not having mannose-1-phosphate transferase activity. This mutant is available as LB1425-1B (MATa mnn6) from Professor Ballou, Berkeley College, California University, U.S.A.

This mutant can further be hybridized in a usual manner with a known yeast mutant having various defects in the sugar chain synthesis steps to introduce a plurality of mutations in the sugar chain synthesis into one cell line. For example, as proposed previously by the present inventors, diploid cells are prepared by crossing a yeast mutant having an OCH1 gene disruption and a mnn1 mutation [Δoch1 mnn1 (FERM P-13219): see Japanese Patent Application LOP Publication No. 277,086/1994] with said mnn6 mutant (mnn6) of different mating type. The cells are then transferred to a nitrogen-free spore formation medium [see e.g. F. Sherman, Methods in Enzymology, vol. 194, p. 17 (1991)] where they yield 4 kinds of spores through meiosis. These spores are separated under a microscope and examined for their genotype so that a triple (Δoc1, mnn1, and mnn6) mutant can be obtained (see e.g. F. Sherman and J. Hicks, Methods in Enzymology, vol.194, pp. 21–37 (1991)).

2. Production of the mannose-1-phosphate-containing acidic sugar chains (FIG. 1, Formulae 2 to 4) and their conversion into phosphate-containing acidic sugar chains (FIG. 1, Formulae 5 to 7)

According to the present invention, it is possible to produce and accumulate the desired mannose-1-phosphate transferase by culturing yeast cells transformed with a plasmid containing said mannose-1-phosphate transferase gene, and it is further possible to obtain the acidic sugar chains having mannnose-1-phosphates added to the neutral core sugar chain. The transformed yeast can be cultured in the same manner as for conventional yeasts. For example, the medium used may be a synthetic medium (containing a carbon source, a nitrogen source, inorganic salts, amino acids, vitamins etc.) prepared by adding certain medium ingredients (available from Difco Co.) except for those amino acids and nucleotides (e.g. uracil) which can be supplied with a marker (e.g. URA3 gene involved in uracil synthesis) necessary for plasmid replication and maintenance (see F. Sherman, Methods in Enzymology, vol. 194, p. 14 (1991)).

Because it is estimated from the amino acid sequence and functions of the desired mannose-1-phosphate transferase that this enzyme produced in transformant cells thus cultured is localized in a membrane fraction of the Golgi apparatus, this membrane fraction is obtained for use as an enzyme source by disrupting the yeast cells, subsequent centrifugation (e.g. 100,000×g, 60 minutes) etc. (see Nakayama et al., EMBO J., vol. 11, pp. 2511–2519 (1992)).

The sugar chains having mannose-1-phosphates added thereto (FIG. 1, Formulae 2 to 4) can be produced using the membrane fraction thus obtained as an enzyme source by reacting GDP-mannose as donor substrate with various neutral sugar chains as receptor substrate in the presence of Mn ions or surface active agents previously reported as enzyme stabilizers (see E. M. Karson and C. E. Ballou, J. Biol. Chem., vol. 253, pp. 6484–6492 (1978)).

The sugar chains produced in this manner can be easily converted in a known method (e.g. mild acid hydrolysis) into the phosphate-containing sugar chains (FIG. 1, Formulae 5 to 7) identical with human-derived acidic sugar chains.

According to the present invention, the acidic sugar chains with mannose-1-phosphate added to the same high mannose type neutral sugar chain as produced by mammalian (e.g. human) cells can be produced in large amounts with high purity by genetic engineering means.

Furthermore, effective drug delivery is expected by allowing the phosphate-containing core sugar chains to be present in encapsulation, into liposomes, of a drug useful for treatment of lysosome enzyme deficiency in humans so that the drug can be concentrated in lysosomes in cells. For this purpose, the acidic sugar chains identical with the human-derived phosphate-containing core sugar chains can be produced in large amounts with high purity according to the present invention.

EXAMPLES

The present invention is specifically described by reference to the following examples which are not intended to limit the scope of the present invention.

[Example 1]

Preparation of a triple mutant (Δoch1 mnn1 mnn6) having Δoc1, mnn1, and mnn6 mutations A yeast Δoch1 mutant lacks the addition reaction of a first α-1,6-bound mannose molecule through which a mannose outer chain is added to the core sugar chain of glycoprotein, and a yeast mnn1 mutant lacks the addition reaction of a mannose molecule via α-1,3-linkage to the non-reduced terminals of the core sugar chain and of the outer sugar chain branch. A double mutant (Δoch1 mnn1) having said two mutations produces the neutral core sugar chain (Man$_8$GlcNAc$_2$) as suggested by the present inventors (Japanese Patent Application LOP Publication No. 277,086/1994). However, this mutant was observed to further produce an acidic sugar chain containing mannose-1-phosphate in addition to said neutral core sugar chain. Hence, a triple mutant having 3 mutations (Δch1, mnn1, and mnn6) was prepared as a strain producing only the uniform neutral core sugar chain free from mannose-1-phosphate. Because this triple mutant is expected to contain less mannose-1-phosphate than does the double mutant (Δoch1 mnn1), it was considered that triple mutant cells are hardly stained blue with basic dye Alcian Blue-8GX (produced by Sigma, Code No. A3157) i.e. a dye readily binding to acidic group containing negative charge. Hence, the triple mutant cells were selected with this dye on the basis of their less stainability.

A YNS3-7A strain (MAT αΔoch1 mnn1 his1 and/or his3 ura3) was prepared from Saccharomyces cerevisiae YN3-1D (MAT αΔoch1 mnn1 his1 and/or his3) by conferring ura3 mutation thereon with 5'-fluoroorotic acid (see Japanese Patent Application LOP Publication No. 277,086/1994). This strain was crossed with mnn6 mutant strain LB1425-1B (MATa mnn6) (obtained from Professor Ballou, Berkeley College, California University, U.S.A.), and haploid cells were obtained through meiosis and selected for desired triple mutants T05-2B (MATαΔoch1 mnn1 mnn6 his1 and/or his3 ura3) and T05-6C (MATαΔoch1 mnn1 mnn6 ura3). Further, a triple mutant TO3-6D (MATa leu2 ura3 his1 and/or his3 mnn1 mnn6) and a double mutant T05-2C (Δoch1 mnn1 ura3) were prepared in the same manner as above.

Said triple mutant T05-2B (MAT αΔoch1 mnn1 mnn6 his1 and/or his3 ura3) was designated S. cerevisiae T05-2B and deposited as FERM BP-5294 with the National Institute of Bioscience and Human-Technology, Agency of Industrial Science and Technology, Japan.

[Example 2]

Isolation of the MNN6 gene by use of its adsorbability to alcian blue dye $1.1 \times 10^8$ mnn6 mutant T03-6D cells (MATa leu2 ura3 his1 and/or his3 mnn1 mnn6) (for their preparation, see [Example 1]) were transformed by the lithium method (Ito et al., J. Bacteriol., vol. 153, pp. 163–168, 1983) with 110 µg yeast chromosomal DNA library ("GENE BANK" A and B purchased from American Type Culture Collection (ATCC)) constructed on single copy vector YCp50 containing URA3 marker. After transformation, the cells were plated on an SD-Ura plate (2% glucose, 0.67% Yeast Nitrogen Base w/o amino acids (produced by Difco Co.), 0.3M sorbitol, a mixture of nucleic acids (excluding uracil) and amino acids (20–400 μg/ml)) and then cultured at 30° C. for 2 days to give 1.2×10$^4$ colonies. A nitrocellulose filter was overlaid on the colonies, then placed as the replica on another SD-Ura plate, and incubated for 1 day at 30° C. The nitrocellulose filter was autoclaved at 120° C. for 1 hour whereby the colonies were immobilized on the filter. This nitrocellulose filter was stained for 20 to 30 minutes with 0.1% alcian blue in 10 ml of 0.02N HCl at room temperature (Ballou, C. E., Methods in Enzymology, 185, 440–470, 1990). This staining indicated that the majority of colonies were white, and 2 colonies colored with blue were isolated as positive clones.

Figure 2:
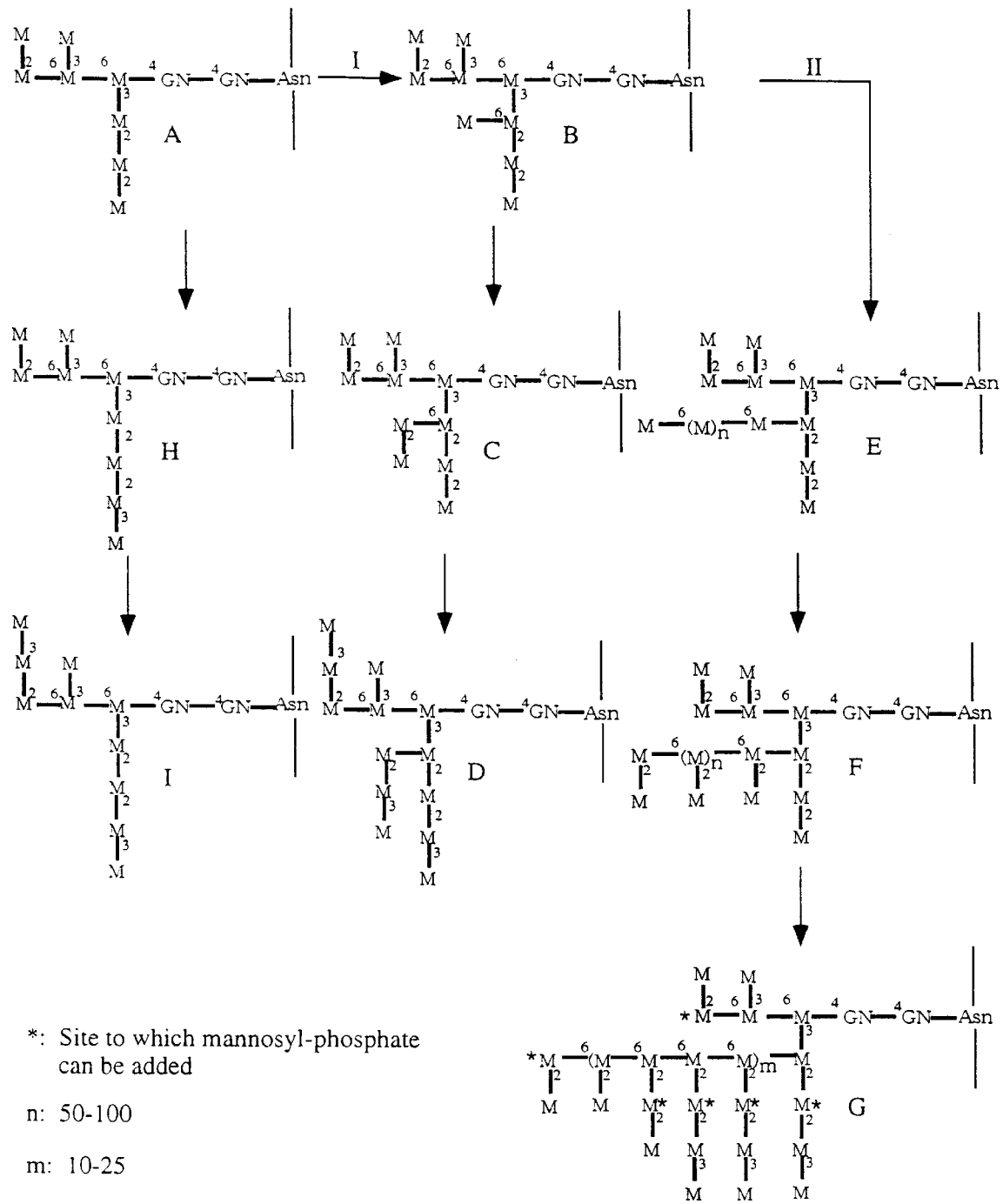
FIG. 2 shows a pathway of addition of mannose to the core sugar chain of an N-linked sugar chain in yeast.
Figure 3:
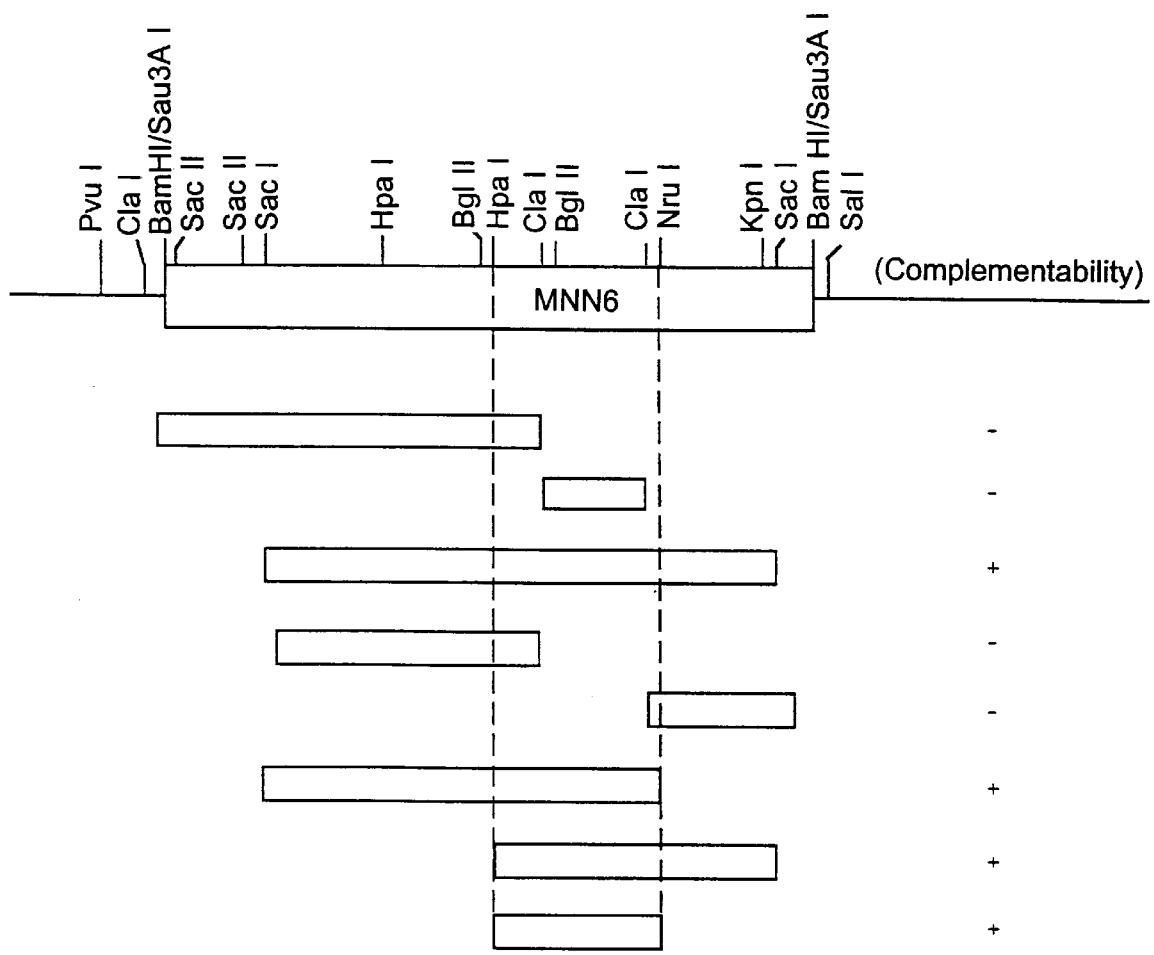
FIG. 3 shows a restriction enzyme map of DNA fragments containing the isolated MNN6 gene and the complementability of the DNA fragments to mnn6 mutation.

From the isolated 2 colonies, their plasmids were recovered. T03-6D strain, not liable to blue-staining by itself, was transformed with this plasmid and then examined for stainability with alcian blue. For alcian blue staining, a culture of the yeast grown in 1.5 ml SD-Ura medium was centrifuged at 15,000 r.p.m. The yeast thus precipitated was washed with water, followed by addition of 0.1% alcian blue in 0.5 ml of 0.02N HCl. It was stirred and left for 15 minutes at room temperature. Thereafter, the yeast was precipitated by centrifugation at 15,000 r.p.m. and then examined for stainability with alcian blue dye. As a result, T03-6D strain into which the plasmid was introduced became stained blue with alcian blue. The 2 kinds of plasmid from the 2 positive colonies were examined for their inserts. The result indicated that both of the plasmids carry an about 10 kb fragment containing the same restriction enzyme sites (FIG. 3). This insert was further cleaved and various fragments were examined for their complementability to mnn6 mutation. The result indicated that an about 2.6 kbp HpaI-NruI fragment is the minimum fragment for complementing mnn6 mutation (FIG. 3).

[Example 3]
Determination of the nucleotide sequence of the MNN6 gene

Figure 4:
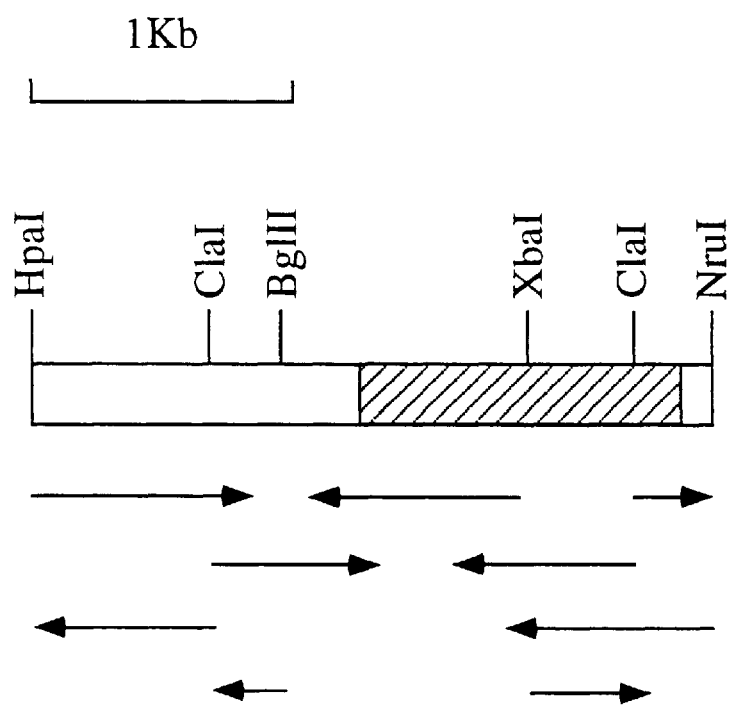
FIG. 4 shows a method of determining the DNA nucleotide sequence containing the MNN6 gene.

The MNN6 gene, about 2.6 kb, was cleaved with restriction enzymes and inserted into yeast-*E. coli* shuttle vector pRS316. The resulting plasmids into which various MNN6 gene fragments were inserted were sequenced in an automatic sequencer produced by Licor Co. (LI-COR Model 4000L) using M13 universal M13 primer and SeruiThem Long-Read Cycle Sequencing Kit-LC (FIG. 4). The nucleotide sequence thus determined suggested that the MNN6 gene codes for a protein consisting of 446 amino acid residues. This protein possessed a hydrophobic region capable of membrane-spanning near the N-terminus (FIG. 5).

*E. coli* JM109 carrying plasmid pRS-MNN6 containing the MNN6 gene integrated into it was designated *E. coli* JM109/pRS-MNN6 and deposited as FERM BP-5295 with the National Institute of Bioscience and Human-Technology, Agency of Industrial Science and Technology, Japan.

[Example 4]
Construction of MNN6 gene expression vector and preparation of a yeast transformant carrying the plasmid The about 2.6 kb fragment containing the MNN6 gene (HpaI-NruI) was cleaved with restriction enzymes and inserted into an SmaI site of yeast-*E. coli* shuttle vector pRS316 containing URA3 marker whereby pRS-MNN6 was constructed. This pRS-MNN6 was transformed into the triple mutant T05-2B (Δoch1 mnn1 mnn6 his1 and/or his3 ura3) (see [Example 1]) prepared by introducing mnn6 mutation to the double mutant lacking in the mannosyltransferase gene (OCH1) forming an outerchain for yeast N-linked type sugar chain and having a mutation on the mannosyltransferase gene (MNN1) transferring the terminal α-1,3-mannose. The resulting transformant was designated T05-2B/pRS-MNN6.

[Example 5]
Measurement of mannose-1-phosphate transferase activity by use of a microsome membrane fraction of MNN6 gene transformant T05-2B/pRS-MNN6 obtained above, T05-2B/pRS316 (i.e. the triple mutant transformed with the control plasmid), and double mutant T05-2C (Δoch1 mnn1 ura1) not having mnn6 mutation were respectively grown until their mid-logarithmic growth phase (Klett value 200) at 25° C. in 200 ml synthetic SD-Ura medium or natural YPD medium (2% Bacto pepton, 1% yeast extract, 2% glucose) (produced by Difco Co.) and then centrifuged 5,000×g, 10 minutes to collect yeast cells. The cells were washed with 1% KCl and suspended in 5 ml Lysis Buffer (50 mM Tris-HCl pH 7.5, 10 mM MnCl$_2$, 5% glycerol, 1 mM PMSF, 2 μg/ml antipain, chymostatin, leupeptin, pepstatin A), and glass beads (diameter 0.45–0.50 mm) were added thereto until the beads reached half of the total volume, and the vessel was cooled at −20° C. for 1 hour. Thereafter, the cells were disrupted for 1 minute by a cell homogenizer produced by B. Broun Co. and then the disrupted cells were left for 1 minute. The disrupted cells were further disrupted twice in the same manner. Then, the glass beads were removed through a G1 glass filter, and the remaining solution containing the disrupted cells were centrifuged for 5 minutes at 3,000×g to remove the cell debris. The supernatant was further centrifuged for 20 minutes at 10,000×g, and the precipitates were recovered as low speed pellet (LSP). The remaining supernatant was further centrifuged at 100,000×g for 1 hour to give precipitates as high speed pellet (HSP). The LSP and HSP fractions were suspended respectively in Lysis Buffer, and their protein contents were determined with BCA protein determination kit produced by Pierce Co. Their mannosyl phosphate transferase activity was also determined according to the measurement method of Och1p i.e. mannosyltransferase from yeast (Nakayama et al., EMBO J., vol. 11, pp. 2511–2519 (1992)).

400 μg (in terms of protein) of the above membrane fraction was allowed to react at 30° C. for 1 hour in 50 μl of 50 mM Tris-HCl, pH 6.0 containing 10 mM MnCl$_2$, 0.06% Triton X100, 1 μM Man$_8$GlcNAc$_2$-PA, 1 mM GDP-mannose, 0.5 mM 1-deoxy-mannojirimycin. The enzyme was inactivated by heating the reaction solution at 100° C. for 5 minutes. To remove high molecular substances, the solution was passed through ultrafree C3LGC (cut off molecular weight of 10,000), and the filtrate was analyzed by HPLC as follows.

In HPLC, an amino column Asahipak NH2P-50 (4.6×250 mm) was used. The solvent used was a 7:3 mixture (solution A) of acetonitrile and 200 mM acetate-triethylamine (pH 7.3) and a 3:7 mixture (solution B) of acetonitrile and 200 mM acetate-triethylamine (pH 7.3). The elution was carried out at a flow rate of 1 ml/min. in a linear gradient for 40 minutes from 20% of solution B to 100% of solution B. The activity of mannose-1-phophate transferase was calculated from the ratio in area of the reaction products (peaks 2 and 3) (FIG. 6) to Man$_8$GlcNAc$_2$-PA (produced by Takara, Code No. 4119) (peak 1) as sugar receptor.

The result indicated that the mannose-1-phosphate transferase activity was not detected when the membrane fraction from the strain (T05-2B/pRS316) prepared by transforming the triple mutant (having mnn6 mutation) with the control plasmid was used as an enzyme source (FIG. 6, A), while peaks 2 and 3 (=reaction products) were detected in the double mutant (T05-2C) not having mnn6 mutation (FIG. 6, B) and the triple mutant (T05-2B/pRS-MNN6) transformed with the plasmid having one copy of the MNN6 gene (FIG. 6, C). The enzyme activity at this time was about 5 pmol mannose-1-phosphate/mg protein/hr. Hence, the mannose-1-phosphate transferase activity was recovered in proportion to the copy number of the NMM6 gene, so it was made evident by the introduction of the MNN6 gene that it is the gene coding for mannose-1-phosphate transferase itself.

[Example 6]
Structural analysis of the reaction product of mannose-1-phosphate transferase enzyme Two reaction products obtained in the above activity measurement (peaks 2 and 3) (FIG. 6) were analyzed to determine whether they are products having mannose-1-phosphate transferred as desired. First, compounds whose structures were determined by NMR (FIG. 7, Structures B and C) were analyzed in HPLC under the same conditions as in the above activity measurement system. The compound of structure B was eluted at the same position as peak 3 observed in FIG. 6. This suggested that peak 3 has the same sugar chain as structure B. The compound of structure C having 2 molecules of mannose-1-phosphate added thereto was eluted considerably later than peaks 2 and 3. This suggested that peak 2 has structure A having 1 molecule of mannose-1-phosphate added thereto at a different position from that in structure B.

Further, peaks 2 and 3 were directly confirmed to be sugar chains having 1 molecule of mannose-1-phosphate added thereto, as follows. Peaks 2 and 3 were collected and the mannose moiety was cleaved off from the mannose-1-phosphate residue by hydrolysis under mild acid conditions. The solvent in the peak was removed by freeze-drying, and the sample was treated with 0.5 ml of 0.01N HCl at 100° C. for 30 minutes. After removal of the solvent and HCl by freeze-drying, the sample was analyzed in HPLC. The result indicated that both peaks 2 and 3 were eluted at considerably later positions (FIG. 8, B). This was considered due to their increased adsorbability onto the amino column, resulting from the increased charge of the phosphate group owing to the removal of mannose from the mannose-1-phosphate residue. Then, these peaks were treated with alkaline phosphatase as follows. After the solvent was removed by freeze-drying, the sample was dissolved in 40 μl of 50 mM Tris-HCl buffer (pH 9.5). After addition of 0.2 units of alkaline phosphatase, the sample was allowed to react at room temperature for 4 hours. Then, the solvent was removed by freeze-drying and the sample was analyzed in HPLC. The result indicated that these peaks were eluted at the same position as $Man_8GlcNAc_2$-PA (peak 1) used as the sugar receptor (FIG. 8, C). These results revealed that peaks 2 and 3 (FIG. 8, A) have one mannose-1-phosphate molecule added to $Man_8GlcNAc_2$-PA, and that peak 2 is an acidic sugar chain as shown in the structure A in FIG. 7, and peak 3 is an acidic sugar chain as shown in structure B in FIG. 7.

What is claimed is:

1. An isolated nucleic acid from *Saccharomyces cerevisiae* represented by the nucleotide sequence of SEQ ID NO:1.

2. A plasmid DNA comprising
   (a) a mannose-1-phosphate transferase gene from yeast represented by the nucleotide sequence of SEQ ID NO: 1, or
   (b) a portion of said mannose-1-phosphate transferase gene, wherein the portion encodes a polypeptide having mannose-1-phosphate transferase activity.

3. A process for producing a mannose-1-phosphate-containing acidic sugar chain, which comprises culturing yeast cells transformed with plasmid DNA comprising the nucleic acid of claim 1, obtaining mannose-phosphate transferase from the culture and allowing the enzyme to act on a neutral core sugar chain in vivo or in vitro.

4. A process for producing a phosphate-containing acidic sugar chain, which comprises culturing yeast cells transformed with plasmid DNA comprising the nucleic acid of claim 1, obtaining mannose-phosphate transferase from the culture, allowing the enzyme to act on a neutral core sugar chain in vivo or in vitro thereby producing a mannose-1-phosphate-containing acidic sugar chain, and removing a mannose moiety by acid-treatment of the mannose-1-phosphate-containing acidic sugar chain.

* * * * *

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
 ( A ) LENGTH: 1380 base pairs
 ( B ) TYPE: nucleic acid
 ( C ) STRANDEDNESS: single
 ( D ) TOPOLOGY: linear ( i x ) FEATURE:
 ( A ) NAME/KEY: CDS
 ( B ) LOCATION: 1..1339

( x i ) SEQUENCE DESCRIPTION: SEQ ID NO:1:

| ATG | CAC | GTA | CTG | CTG | AGC | AAA | AAA | ATA | GCA | CGC | TTT | CTG | TTG | ATT | TCG | 48 |
|-----|-----|-----|-----|-----|-----|-----|-----|-----|-----|-----|-----|-----|-----|-----|-----|----|
| Met | His | Val | Leu | Leu | Ser | Lys | Lys | Ile | Ala | Arg | Phe | Leu | Leu | Ile | Ser |    |
| 1   |     |     |     | 5   |     |     |     |     | 10  |     |     |     |     | 15  |     |    |

| TTT | GTT | TTC | GTG | CTT | GCG | CTA | ATG | GTG | ACA | ATA | AAT | CAT | CCA | AAA | ACA | 96 |
| Phe | Val | Phe | Val | Leu | Ala | Leu | Met | Val | Thr | Ile | Asn | His | Pro | Lys | Thr |    |
|     |     |     | 20  |     |     |     |     | 25  |     |     |     |     | 30  |     |     |    |

| AAG | CAG | ATG | TCT | GAA | CAG | TAT | GTT | ACA | CCA | TAC | CTT | CCG | AAA | TCT | TTG | 144 |
| Lys | Gln | Met | Ser | Glu | Gln | Tyr | Val | Thr | Pro | Tyr | Leu | Pro | Lys | Ser | Leu |     |
|     |     | 35  |     |     |     | 40  |     |     |     |     | 45  |     |     |     |     |     |

| CAA | CCT | ATT | GCA | AAA | ATT | AGT | GCA | GAG | GAA | CAA | AGG | CGT | ATA | CAA | AGT | 192 |
| Gln | Pro | Ile | Ala | Lys | Ile | Ser | Ala | Glu | Glu | Gln | Arg | Arg | Ile | Gln | Ser |     |
|     | 50  |     |     |     |     | 55  |     |     |     |     | 60  |     |     |     |     |     |

| GAA | CAG | GAA | GAA | GCC | GAA | TTG | AAG | CAA | TCT | TTA | GAG | GGA | GAG | GCC | ATT | 240 |
| Glu | Gln | Glu | Glu | Ala | Glu | Leu | Lys | Gln | Ser | Leu | Glu | Gly | Glu | Ala | Ile |     |
| 65  |     |     |     |     | 70  |     |     |     |     | 75  |     |     |     |     | 80  |     |

| AGA | AAT | GCC | ACC | GTG | AAT | GCC | ATT | AAG | GAA | AAG | ATC | AAA | TCT | TAT | GGT | 288 |
| Arg | Asn | Ala | Thr | Val | Asn | Ala | Ile | Lys | Glu | Lys | Ile | Lys | Ser | Tyr | Gly |     |

-continued

|  |  | 85 |  |  |  |  |  | 90 |  |  |  |  |  | 95 |  |  |  |
|---|---|---|---|---|---|---|---|---|---|---|---|---|---|---|---|---|---|

```
GGT  AAT  GAA  ACG  ACG  CTA  GGG  TTC  ATG  GTG  CCA  TCG  TAT  ATC  AAT  CAT      336
Gly  Asn  Glu  Thr  Thr  Leu  Gly  Phe  Met  Val  Pro  Ser  Tyr  Ile  Asn  His
               100                      105                     110

AGA  GGA  TCA  CCA  CCA  AAG  GCG  TGC  TTT  GTC  TCA  CTA  ATT  ACT  GAA  AGG      384
Arg  Gly  Ser  Pro  Pro  Lys  Ala  Cys  Phe  Val  Ser  Leu  Ile  Thr  Glu  Arg
          115                      120                     125

GAT  TCC  ATG  ACC  CAA  ATC  TTA  CAA  TCT  ATT  GAT  GAA  GTG  CAG  GTG  AAG      432
Asp  Ser  Met  Thr  Gln  Ile  Leu  Gln  Ser  Ile  Asp  Glu  Val  Gln  Val  Lys
     130                      135                     140

TTT  AAC  AAA  AAT  TTT  GCT  TAT  CCT  TGG  GTT  TTT  ATT  AGT  CAG  GGG  GAG      480
Phe  Asn  Lys  Asn  Phe  Ala  Tyr  Pro  Trp  Val  Phe  Ile  Ser  Gln  Gly  Glu
145                      150                     155                      160

CTT  GAC  GGA  ATG  AAG  CAA  GAA  ATG  ATT  CGT  CAA  GCC  ATA  ACT  GAT  TCT      528
Leu  Asp  Gly  Met  Lys  Gln  Glu  Met  Ile  Arg  Gln  Ala  Ile  Thr  Asp  Ser
                     165                      170                     175

ATG  AAT  GGT  GAT  CCT  GAG  TTA  ATT  AAT  ATT  AAA  TTT  GCT  GAA  ATT  CCT      576
Met  Asn  Gly  Asp  Pro  Glu  Leu  Ile  Asn  Ile  Lys  Phe  Ala  Glu  Ile  Pro
                180                      185                     190

GCA  GAC  GAA  TGG  GTA  TAC  CCT  GAA  TGG  ATT  GAT  GAA  AAT  AAA  GCA  GCA      624
Ala  Asp  Glu  Trp  Val  Tyr  Pro  Glu  Trp  Ile  Asp  Glu  Asn  Lys  Ala  Ala
           195                      200                     205

GAA  TCG  CTA  ATT  TCA  TTA  GCA  AAT  GTA  CCG  GAT  GGT  GAT  TCT  AGA  GCT      672
Glu  Ser  Leu  Ile  Ser  Leu  Ala  Asn  Val  Pro  Asp  Gly  Asp  Ser  Arg  Ala
      210                      215                     220

GTA  AGA  TAT  CAA  GCT  AGA  TAT  TTT  GCA  GGG  TTT  TTT  TGG  AGG  CAT  CCA      720
Val  Arg  Tyr  Gln  Ala  Arg  Tyr  Phe  Ala  Gly  Phe  Phe  Trp  Arg  His  Pro
225                      230                     235                      240

GTT  CTG  GAT  GAG  TTT  GAT  TGG  TAC  TGG  AGA  GTA  GAC  CCT  GGT  ATT  AAA      768
Val  Leu  Asp  Glu  Phe  Asp  Trp  Tyr  Trp  Arg  Val  Asp  Pro  Gly  Ile  Lys
                     245                      250                     255

TTG  TAC  TGT  GAT  ATT  GAT  CAT  GAC  CTT  TTT  AGG  TGG  ATG  CAA  GAT  GAA      816
Leu  Tyr  Cys  Asp  Ile  Asp  His  Asp  Leu  Phe  Arg  Trp  Met  Gln  Asp  Glu
                260                      265                     270

GGC  AAA  GTG  TTT  GGT  TTC  ACA  TTG  AGT  ATG  AGT  GAA  GCT  AAG  GAA  GCC      864
Gly  Lys  Val  Phe  Gly  Phe  Thr  Leu  Ser  Met  Ser  Glu  Ala  Lys  Glu  Ala
           275                      280                     285

AAT  GAG  AAG  ATT  TGG  GAT  GTT  ACG  AAA  AAA  TTT  GCA  AAG  GAT  TTT  CCA      912
Asn  Glu  Lys  Ile  Trp  Asp  Val  Thr  Lys  Lys  Phe  Ala  Lys  Asp  Phe  Pro
      290                      295                     300

AAG  TTT  ATT  TCC  GAG  AAT  AAT  TTC  AAG  TCA  TTT  ATT  ACA  AAA  AAG  GAC      960
Lys  Phe  Ile  Ser  Glu  Asn  Asn  Phe  Lys  Ser  Phe  Ile  Thr  Lys  Lys  Asp
305                      310                     315                      320

TCT  GAA  GAT  TTT  AAC  AAC  TGT  GAA  TTC  ACA  TCA  AAT  TTT  GAA  ATT  GGT     1008
Ser  Glu  Asp  Phe  Asn  Asn  Cys  Glu  Phe  Thr  Ser  Asn  Phe  Glu  Ile  Gly
                     325                      330                     335

AAT  TTG  AAC  TTT  TAT  AGA  TCG  CCA  GCT  TAC  AGG  AAA  TTT  TTT  AAT  TAC     1056
Asn  Leu  Asn  Phe  Tyr  Arg  Ser  Pro  Ala  Tyr  Arg  Lys  Phe  Phe  Asn  Tyr
                340                      345                     350

ATC  GAC  GAA  GAG  GGC  GGT  ATT  TTC  TAC  TGG  AAA  TGG  TCT  GAT  TCC  ATC     1104
Ile  Asp  Glu  Glu  Gly  Gly  Ile  Phe  Tyr  Trp  Lys  Trp  Ser  Asp  Ser  Ile
           355                      360                     365

ATC  CAC  ACA  ATT  GGG  TTA  TCG  ATG  CTG  TTG  CCA  AAG  GAT  AAA  ATA  CAT     1152
Ile  His  Thr  Ile  Gly  Leu  Ser  Met  Leu  Leu  Pro  Lys  Asp  Lys  Ile  His
      370                      375                     380

TTT  TTC  GAA  AAT  ATA  GGA  TTC  CAT  TAT  GAC  AAG  TAC  AAT  AAC  TGT  CCC     1200
Phe  Phe  Glu  Asn  Ile  Gly  Phe  His  Tyr  Asp  Lys  Tyr  Asn  Asn  Cys  Pro
385                      390                     395                      400

CTA  AAC  GAT  GAT  ATA  TGG  AAC  CAA  TAT  AAT  TGT  AAC  TGT  GAC  CAG  GGT     1248
Leu  Asn  Asp  Asp  Ile  Trp  Asn  Gln  Tyr  Asn  Cys  Asn  Cys  Asp  Gln  Gly
```

```
                                   405                                      410                                   415
AAC  GAT  TTC  ACG  TTT  AGA  AGT  GGT  TCA  TGT  GGC  GGA  CAT  TAC  TTC  GAC      1296
Asn  Asp  Phe  Thr  Phe  Arg  Ser  Gly  Ser  Cys  Gly  Gly  His  Tyr  Phe  Asp
               420                      425                      430

ATT  ATG  AAG  AAA  GAT  AAG  CCA  GAA  GGT  TGG  GAT  AGG  TTA  CCA  T             1339
Ile  Met  Lys  Lys  Asp  Lys  Pro  Glu  Gly  Trp  Asp  Arg  Leu  Pro
               435                      440                      445

AAATCAAAAC  ACTGATGTAT  AAGAACAATA  ATCTTCTACA  T                                   1380
```

( 2 ) INFORMATION FOR SEQ ID NO:2:

( i ) SEQUENCE CHARACTERISTICS:
        ( A ) LENGTH: 446 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

```
Met  His  Val  Leu  Leu  Ser  Lys  Lys  Ile  Ala  Arg  Phe  Leu  Leu  Ile  Ser
 1                       5                        10                      15

Phe  Val  Phe  Val  Leu  Ala  Leu  Met  Val  Thr  Ile  Asn  His  Pro  Lys  Thr
               20                       25                       30

Lys  Gln  Met  Ser  Glu  Gln  Tyr  Val  Thr  Pro  Tyr  Leu  Pro  Lys  Ser  Leu
               35                       40                       45

Gln  Pro  Ile  Ala  Lys  Ile  Ser  Ala  Glu  Gln  Arg  Arg  Ile  Gln  Ser
      50                       55                       60

Glu  Gln  Glu  Glu  Ala  Glu  Leu  Lys  Gln  Ser  Leu  Glu  Gly  Glu  Ala  Ile
 65                      70                       75                       80

Arg  Asn  Ala  Thr  Val  Asn  Ala  Ile  Lys  Glu  Lys  Ile  Lys  Ser  Tyr  Gly
               85                       90                       95

Gly  Asn  Glu  Thr  Thr  Leu  Gly  Phe  Met  Val  Pro  Ser  Tyr  Ile  Asn  His
               100                      105                      110

Arg  Gly  Ser  Pro  Pro  Lys  Ala  Cys  Phe  Val  Ser  Leu  Ile  Thr  Glu  Arg
               115                      120                      125

Asp  Ser  Met  Thr  Gln  Ile  Leu  Gln  Ser  Ile  Asp  Glu  Val  Gln  Val  Lys
      130                      135                      140

Phe  Asn  Lys  Asn  Phe  Ala  Tyr  Pro  Trp  Val  Phe  Ile  Ser  Gln  Gly  Glu
145                      150                      155                      160

Leu  Asp  Gly  Met  Lys  Gln  Glu  Met  Ile  Arg  Gln  Ala  Ile  Thr  Asp  Ser
               165                      170                      175

Met  Asn  Gly  Asp  Pro  Glu  Leu  Ile  Asn  Ile  Lys  Phe  Ala  Glu  Ile  Pro
               180                      185                      190

Ala  Asp  Glu  Trp  Val  Tyr  Pro  Glu  Trp  Ile  Asp  Glu  Asn  Lys  Ala  Ala
               195                      200                      205

Glu  Ser  Leu  Ile  Ser  Leu  Ala  Asn  Val  Pro  Asp  Gly  Asp  Ser  Arg  Ala
      210                      215                      220

Val  Arg  Tyr  Gln  Ala  Arg  Tyr  Phe  Ala  Gly  Phe  Phe  Trp  Arg  His  Pro
225                      230                      235                      240

Val  Leu  Asp  Glu  Phe  Asp  Trp  Tyr  Trp  Arg  Val  Asp  Pro  Gly  Ile  Lys
               245                      250                      255

Leu  Tyr  Cys  Asp  Ile  Asp  His  Asp  Leu  Phe  Arg  Trp  Met  Gln  Asp  Glu
               260                      265                      270

Gly  Lys  Val  Phe  Gly  Phe  Thr  Leu  Ser  Met  Ser  Glu  Ala  Lys  Glu  Ala
               275                      280                      285

Asn  Glu  Lys  Ile  Trp  Asp  Val  Thr  Lys  Lys  Phe  Ala  Lys  Asp  Phe  Pro
               290                      295                      300
```

| | | | | | | | | | | | | | | |
|---|---|---|---|---|---|---|---|---|---|---|---|---|---|---|
| Lys 305 | Phe | Ile | Ser | Glu | Asn 310 | Asn | Phe | Lys | Ser | Phe 315 | Ile | Thr | Lys | Lys | Asp 320 |
| Ser | Glu | Asp | Phe | Asn 325 | Asn | Cys | Glu | Phe | Thr 330 | Ser | Asn | Phe | Glu | Ile 335 | Gly |
| Asn | Leu | Asn | Phe 340 | Tyr | Arg | Ser | Pro | Ala 345 | Tyr | Arg | Lys | Phe | Phe 350 | Asn | Tyr |
| Ile | Asp | Glu 355 | Glu | Gly | Gly | Ile | Phe 360 | Tyr | Trp | Lys | Trp | Ser 365 | Asp | Ser | Ile |
| Ile | His 370 | Thr | Ile | Gly | Leu | Ser 375 | Met | Leu | Leu | Pro | Lys 380 | Asp | Lys | Ile | His |
| Phe 385 | Phe | Glu | Asn | Ile | Gly 390 | Phe | His | Tyr | Asp | Lys 395 | Tyr | Asn | Asn | Cys | Pro 400 |
| Leu | Asn | Asp | Asp | Ile 405 | Trp | Asn | Gln | Tyr | Asn 410 | Cys | Asn | Cys | Asp | Gln 415 | Gly |
| Asn | Asp | Phe | Thr 420 | Phe | Arg | Ser | Gly | Ser 425 | Cys | Gly | Gly | His | Tyr 430 | Phe | Asp |
| Ile | Met | Lys 435 | Lys | Asp | Lys | Pro | Glu 440 | Gly | Trp | Asp | Arg | Leu 445 | Pro | | |